United States Patent [19]

Sabbaghian et al.

[11] Patent Number: 5,152,771
[45] Date of Patent: Oct. 6, 1992

[54] VALVE CUTTER FOR ARTERIAL BY-PASS SURGERY

[75] Inventors: Mehdy Sabbaghian, Baton Rouge; Russell S. Dailey, Metairie; Gregory T. Dobson, Baton Rouge, all of La.; Hing W. Tang, Perak, Malaysia; Glen J. Schwartzberg, Baton Rouge, La.

[73] Assignees: The Board of Supervisors of Louisiana State University; Agricultural and Mechanical College, both of Baton Rouge, La.

[21] Appl. No.: 636,268

[22] Filed: Dec. 31, 1990

[51] Int. Cl.$^5$ .............................................. A61B 17/32
[52] U.S. Cl. ..................................... 606/159; 606/198
[58] Field of Search ............... 606/159, 167, 172, 170, 606/198, 7; 604/22, 105

[56] References Cited

U.S. PATENT DOCUMENTS

| | | | |
|---|---|---|---|
| 833,759 | 10/1906 | Sourwine | 604/105 |
| 2,816,552 | 12/1957 | Hoffman | 606/159 |
| 4,493,321 | 1/1985 | Leather | 606/159 |
| 4,793,359 | 12/1988 | Sharrow | 606/7 X |
| 4,952,215 | 8/1990 | Ouriel et al. | 606/170 X |
| 4,994,067 | 2/1991 | Summers | 606/170 X |
| 5,069,679 | 12/1991 | Taheri | 606/159 |
| 5,087,264 | 2/1992 | Miller et al. | 606/159 |

FOREIGN PATENT DOCUMENTS 2804015 8/1979 Fed. Rep. of Germany ...... 606/159

*Primary Examiner*—Michael H. Thaler
*Attorney, Agent, or Firm*—William D. Kiesel; Robert C. Tucker

[57] ABSTRACT

A valve cutter for arterial bypass surgery is provided and includes a blade assembly for cutting the venous valves, a shaft for guiding the blade assembly through the bypass vein, an expansion means for preventing the blade assembly from contacting the walls of the bypass vein and for helping to propagate the incisions made in the valve leaflets by the blade assembly, and a control means for controlling the expansion and contraction of the expansion means in order to allow for use of the invention in a variety of bypass vein diameter sizes.

4 Claims, 3 Drawing Sheets

VALVE CUTTER FOR ARTERIAL BY-PASS SURGERY

BACKGROUND OF THE INVENTION

1. Field of the Invention

The present invention relates generally to devices used for in situ arterial bypass surgery where the operation requires that the valves within the bypass vein be cut and disabled to allow the free flow of blood to the lower extremities.

2. Prior Art

In the field of vascular surgery, the surgeon is sometimes confronted by patients experiencing blood flow problems in the lower extremities. If gone uncorrected, the inevitable result is often tissue death necessitating amputation of the limb. Whether this condition is due to past trauma to the arteries or some other atherosclerotic occlusive disease, a common solution is bypass surgery. Such an operation attempts to bypass the normal functioning of the femoropopliteal arterial system by using one of the saphenous veins as a conduit for arterial bypass surgery. Regardless of the method chosen, the existence of valves in these veins is of major concern.

Because the function of the venous system, as opposed to the arterial system, is to return the deoxygenated blood to the heart and lungs, the venous flow of blood in the lower extremities must overcome the force of gravity to allow blood to reach the heart and lungs and stop the downward flow of blood. To accomplish this, the deep veins of the extremities contain numerous valves which prevent retrograde flow. These valves are actually two semicircular shaped leaflets which are attached to the wall of the vein and are part of the interior endothelial lining of the vessel. When blood is flowing normally, the valves lie close against the vessel wall to allow for circulation. This venous flow of blood is dependent upon the calf muscle pump. With contraction of the deep muscles of the leg, a column of blood is advanced past the next set of valves on the way to the heart and lungs. Consequently, any bypass operation that seeks to use a vein in this area as a substitute conduit for arterial circulation must succeed in eliminating the effect of these venous valves.

One method of arterial bypass is to completely remove a section of the saphenous vein and reverse it to put the open position of the valves in the desired direction of blood flow. While this is a potentially feasible or acceptable technique, it is also a traumatic one. The vein walls are extremely sensitive to handling, lack of blood, and temperature and react to such stimuli by strong contractions resulting in severe venospasms. In addition to damage to the endothelium, the natural tapering of the vessel is transposed and the blood now flows from the narrow end to the larger end. There is evidence that the undesirable turbulent flow characteristics of this arrangement is in some way responsible for the development of intimal hyperplasia reported after such operations.

An alternative to the excision and reversal method of bypass surgery is the rerouting of the vein and disablement of the venous valves in situ, or without dissection of the vein from its natural position. This procedure can be performed through several means, one of which is the use of small scissors inserted through venotomies near the location of the valve to be disabled. The disadvantage of such a method is that many incisions must be made, and visualization of the valve site is necessary to avoid cutting the wall of the vessel or accidentally entering one of the side branches present at all valve sites.

A further alternative is the use of a tool called a valvulotome, sometimes referred to as a Mills cutter. This device is essentially a slightly flexible rod with an orthogonal cutting edge used to make an incision on each leaflet of the valve. A venotomy is performed either on a side branch or on the vein itself, and the valvulotome is inserted into the vessel until it is above the valve in the direction of blood flow. One leaflet is severed by pulling back against the valve, and the device is rotated 180° to sever the other leaflet. As with the scissoring method, the process involves numerous punctures into the vein wall to disable the many valves that may be present. It is also time consuming and requires a high degree of precision to successfully perform the operation due to the possibility of cutting other venous tissue.

Ideally, a venous valve cutter should allow for in situ disablement of the valves without the need for a long incision to expose the entire length of the vein used for bypass circulation. It should be capable of insertion at a distal point of the subject vein and guided easily above the first valve to be cut without danger to the sensitive endothelial lining of the vessel. Such a device should also have a means to allow for use of the valve cutter in a wide range of vein diameter sizes, and should not require any rotation of the device in assuring that each valve is successfully disabled in one pass.

SUMMARY OF THE PRESENT INVENTION

Therefore, it is an object of this invention to provide a valve cutter which prevents damage to the walls and side branches of the vessel, while effectively disabling the valves for in situ arterial bypass surgery in only one pass of the instrument.

Another object of this invention is to provide a valve cutter with a disposable cutting member to ensure sterility and efficiency in cutting the valve tissue.

It is also an object of this invention to provide a valve cutter which will operate in a variety of vessel sizes by incorporation of an infinitely adjustable means for clearing the vessel walls from passage of the blade assembly.

A further object of this invention is to provide a valve cutter which is capable of performing valve incisions simply, reliably and without the need for complete exposure of the bypass vessel during the operation or any incision on the proximal end of the vein other than what is necessary to complete the arterial bypass operation.

Other objects, advantages and novel features of the present invention will become apparent to those skilled in the relevant art and to others from the following detailed description of the invention when considered in conjunction with the accompanying drawings.

Accordingly, a valve cutter for cutting the valves in a blood vessel is disclosed comprising a blade assembly for piercing the valves and then cutting the valves in a direction away from the endothelium of the vessel; a shaft to which the blade assembly is attached for guiding the blades through the bypass vein; an adjustable upper spring assembly operatively attached to the shaft for expanding the vein as the valve cutter is inserted into the vein, for preventing the blade assembly from contacting the vessel wall, and to assist in propagating the incisions made in the valve leaflets upon retraction of the valve cutter; an adjustable lower spring assembly for expanding the vein immediately prior to cutting the valve as the valve cutter is retracted from the blood vessel; and a control means for adjusting the expansion and contraction of the upper and lower spring assemblies to accommodate a variety of vessel diameters.

PREFERRED EMBODIMENT OF THE INVENTION

Figure 1:
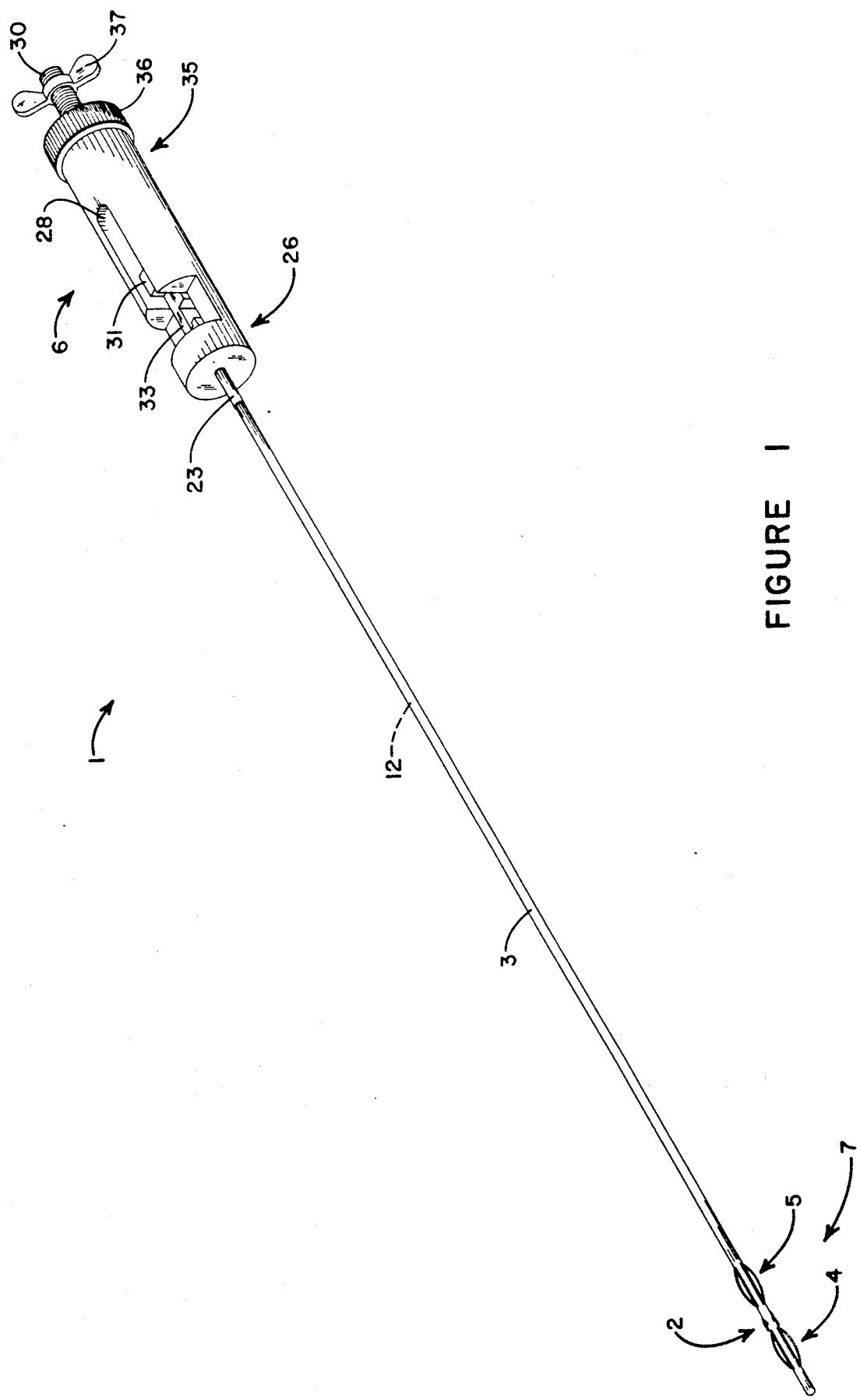
FIG. 1 is an overall view of the valve cutter showing its major components.

FIG. 1 shows an overall view of an assembly of elements used in a preferred embodiment of the valve cutter 1. In its simplest embodiment, the valve cutter 1 consists of a blade assembly 2, a shaft 3, and an expansion means 7. The blade assembly 2 is attached to the shaft 3 and is used to severe to unwanted valves 9 as the shaft 3 is pulled through the bypass vein 8. The expansion means 7 makes contact with the bypass vein 8 so that the blade assembly 2 does not cut anything but the venous valves 9. FIG. 1, however, is the preferred embodiment of the invention in that the blade assembly 2 attached to the shaft 3 is in turn secured to a control means 6. An upper spring assembly 4 and a lower spring assembly 5 are positioned on either side of the blade assembly 2 and are in communication with the control means 6 by way of the shaft 3 and a control wire 12. The shaft 3 is secured to the control means 6 through the use of a sleeve 23 permanently fixed within a sleeve bore 24 on the front end 26 of the control means 6. The tension in the control wire 12 acting between the control means 6 and the upper and lower spring assemblies 4 and 5 helps to retain the shaft 3 within the sleeve 23.

Figure 2:
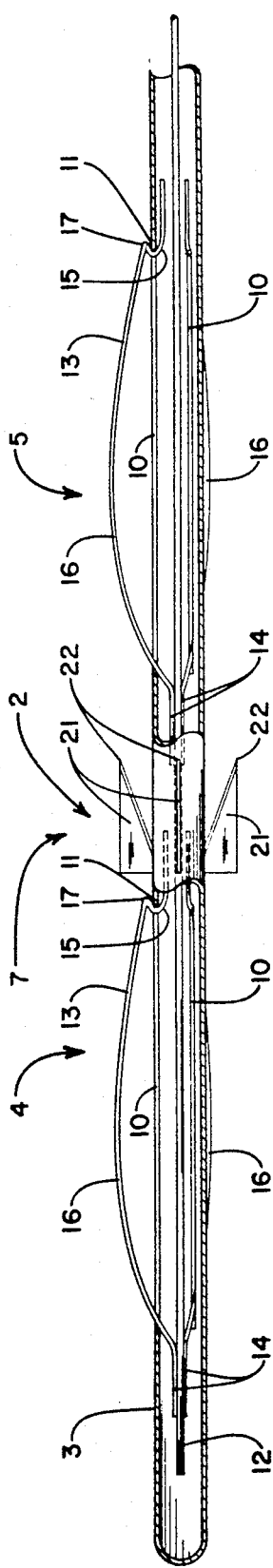
FIG. 2 is a sectional view of the blade assembly as it relates to the upper and lower adjustable spring assemblies.

FIG. 2 is a sectional view of the blade assembly 2 and the expansion means 7 consisting of the upper and lower spring assemblies 4 and 5. The shaft 3 has two sets of three spring slots 10 equally spaced about the circumference of the shaft 3. One set existing above the blade assembly 2 is the upper spring assembly 4 and the other set below the blade assembly z is the lower spring assembly 5. A leaf spring 13 communicates within each spring slot 10 by way of a hook portion 15 formed in the leaf spring base 17. The hook portion 15 is pivotally and resiliently biased against the lower edge 11 of the spring slot 10, while a straight portion 14 is fixedly attached to the control wire 12, thus allowing the spring body 16 to protrude through the spring slot 10 in the shaft 3. The blade assembly z includes four polygonal blades 21 equally spaced about the shaft 3 and each having a blade tip 22 and pointing toward the control means 6 and which have a blade edge 20 extending from the blade tip 22 to the outer surface 34 of the shaft 3. The blade assembly 2 is placed directly and immediately below the upper spring assembly 4.

Figure 3:
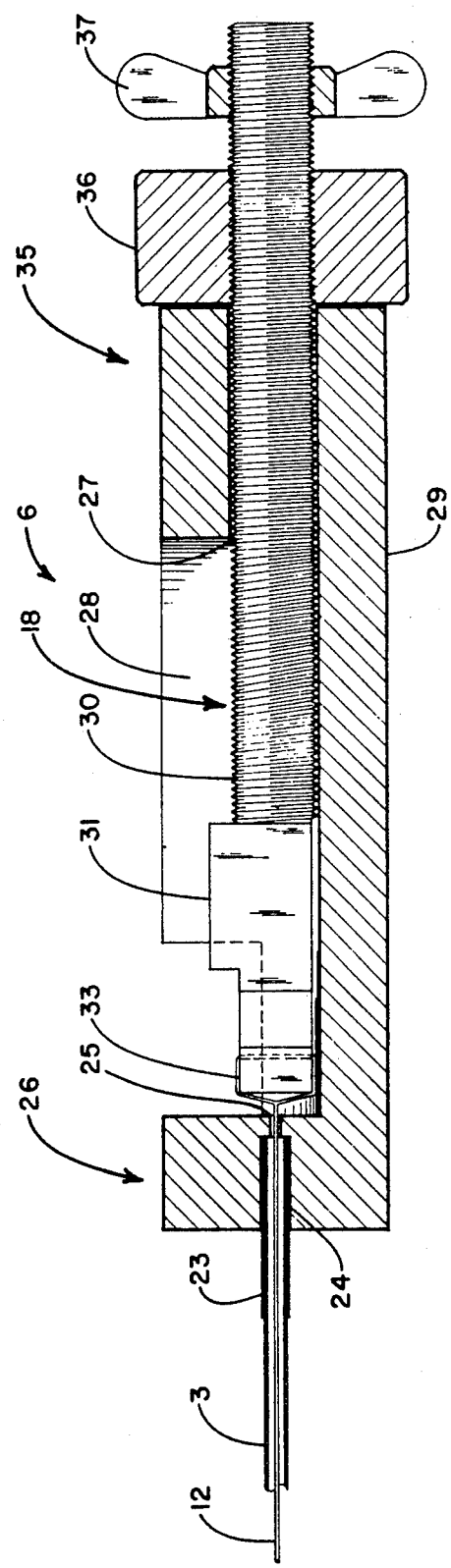
FIG. 3 is a sectional view of the control means.

In FIG. 3, the control means 6 is shown in a sectional view and depicts the method of adjustment of the upper and lower spring assemblies 4 and 5 in a preferred embodiment. The control means 6 includes a controller housing 29 comprising a front end 26 through which is formed a wire bore 2S concentric with but recessed within a sleeve bore 24, and a tension control means 18 The tension control means 18 consists generally of a wire holding means 33, a control screw 30, a screw bore 27, and a control nut 36. A sleeve 23 is permanently secured within the sleeve bore 24 and removably holds the shaft 3 at an end opposite the blade assembly 2. The control wire 12 exiting the shaft 3 passes through the wire bore 25 and is removably secured to wire holding means 33. The wire holding means 33 is fixedly attached to control screw 30 and is prevented from rotating by the use of a screw guide 31 formed as a part of the control screw 30. The rear end 35 of the control means 6 includes a screw bore 27 formed along the longitudinal axis of the controller housing 29, through which the control screw 30 is in slidable communication. To prevent rotation of the control screw 30 and wire holding means 33, the screw guide 31 is also in slidable communication with a guide channel 28 formed in the rear end 35 of the controller housing 29 and parallel to the screw bore 27.

To adjust the tension in the control wire 12, and thus to control the expansion and contraction of the upper and lower spring assemblies 4 and 5, a threaded control nut 36 is biased against the rear end 35 of the controller housing 29 by the tension in the control wire 12. To prevent further movement of the control nut 36, a lock nut 37 is provided to ensure a fixed expansion of the upper and lower spring assemblies 4 and 5.

Figure 4:
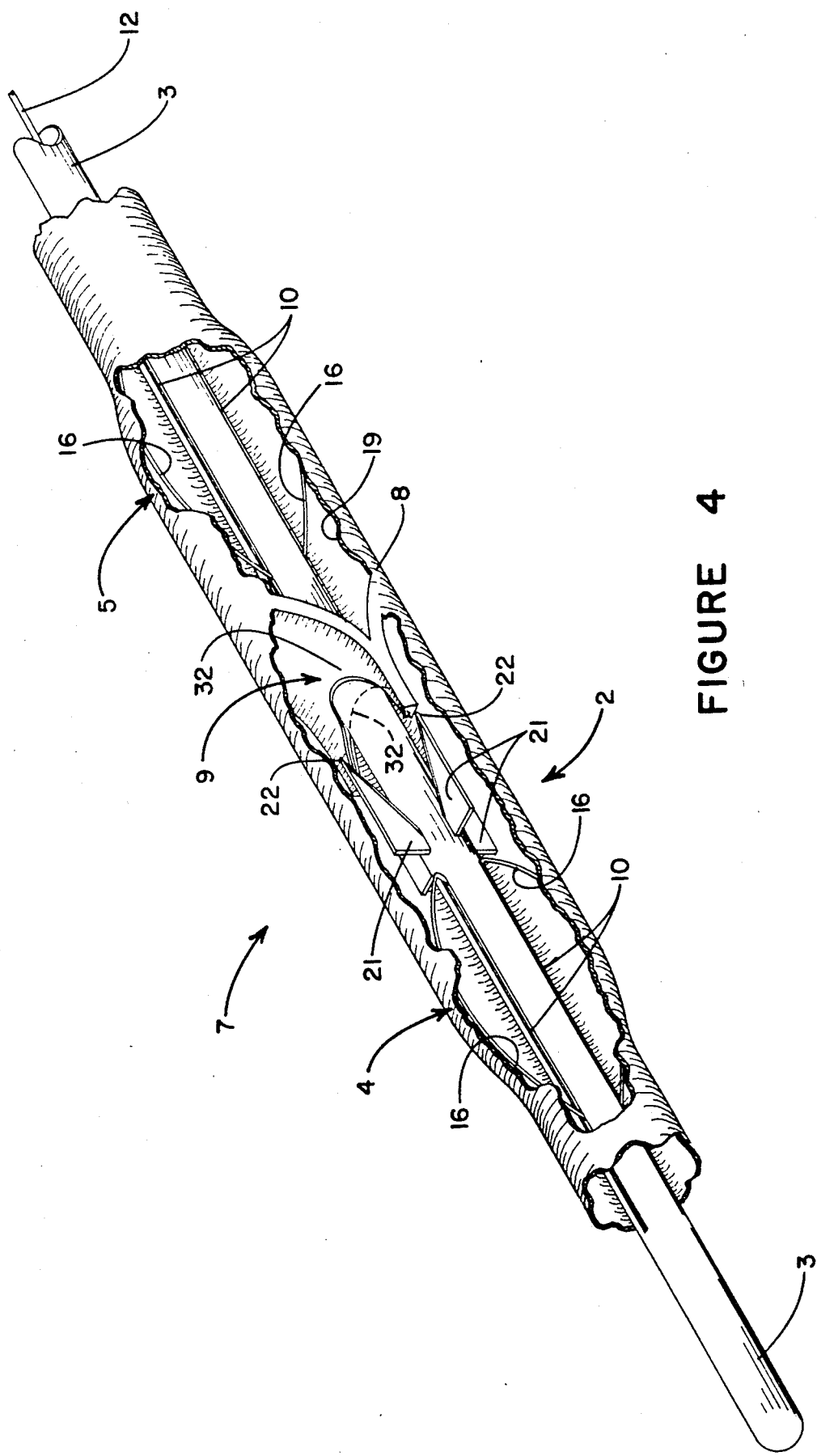
FIG. 4 is sectional view of a bypass vein with the valve cutter in operation immediately before making an incision of the venous valve.

FIG. 4 is a sectional view of the valve cutter 1 inserted into a bypass vein 8 with the blade assembly 2 immediately above a venous valve 9 to be severed. As blood is fills the vein 8, the vessel walls 19 are expanded and the leaflets 32 of the valve 9 close upon the shaft 3 of the valve cutter 1. The lower spring assembly 5 acts to keep the vessel walls 19 away from the blade assembly 2 as the blades 21 approach the valve 9. In this position, the upper spring assembly 4 assists in the expansion of the bypass vein 8, and the valve cutter 1 is slowly pulled through the valve 9 allowing for piercing of the valve 9 by the blade tips 22 and severing the leaflets 32 away from the vessel wall 19. When the blade assembly 2 has passed completely through the valve 9, the upper spring assembly 4 helps to propagate the incisions made by the blade assembly 2, and the blood will flow down to the next valve 9 to be cut. Once all valves 9 are severed, the valve cutter 1 is removed and the remainder of the bypass procedure is completed by methods known to those skilled in the surgical arts.

Many other variations, modifications, and alternate embodiments may be made in the apparatus and techniques hereinbefore described, by those having experience in this technology, without departing from the concept of the present invention. Accordingly, it should be clearly understood that the apparatus and methods depicted in the accompanying drawings and referred to in the foregoing description are illustrative only and are not intended as limitations on the scope of this invention, as defined in the following claims.

What we claim is:

1. A device for cutting the valves in a blood vessel, comprising:
   (a) a blade assembly shaped to pierce said valves and then cut said valves in a single pass and in a direction away from the walls of said blood vessel;
   (b) a shaft to which said blade assembly is attached for guiding said blade assembly through said blood vessel; and (c) an expansion means for expanding said blood vessel and for allowing blood to pass therethrough as said blade assembly is inserted through and retracted from said blood vessel to prevent said blade assembly from contacting said walls of said blood vessel, said expansion means comprising:
  (i) an upper spring assembly attached to said shaft for expanding said blood vessel as said blade assembly is inserted through said blood vessel to prevent said blade assembly from contacting said walls of said blood vessel, and for assisting in propagating the cuts made in said valves upon retraction of said blade assembly; and
  (ii) a lower spring assembly for expanding said blood vessel immediately prior to cutting said valves as said blade assembly is retracted from said blood vessel;

and wherein said upper and lower spring assemblies comprise two groups of three or more leaf springs operatively attached at equal angular distances about the circumference of said shaft, one said group being immediately above said blade assembly and the other said group being immediately below said blade assembly, each said leaf spring having a spring body extending away from said shaft for making expansive contact with said walls of said blood vessel.

2. A device for cutting the valves in a blood vessel, comprising:
 (a) a blade assembly shaped to pierce said valves and then cut said valves in a single pass and in a direction away from the walls of said blood vessel;
 (b) a shaft formed from a rigid hollow tube to which said blade assembly is attached for guiding said blade assembly through said blood vessel;
 (c) an adjustable expansion means for expanding said blood vessel and for allowing blood to pass therethrough as said blade assembly is inserted through and retracted from said blood vessel to prevent said blade assembly from contacting said walls of said blood vessel, said expansion means comprising:
   (i) an upper spring assembly attached to said shaft for expanding said blood vessel as said blade assembly is inserted through said blood vessel to prevent said blade assembly from contacting said walls of said blood vessel, and for assisting in propagating the cuts made in said valves upon retraction of said blade assembly; and
   (ii) a lower spring assembly for expanding said blood vessel immediately prior to cutting said valves as said blade assembly is retracted from said blood vessel;
 (d) control means operatively attached to said adjustable expansion means for controlling the expansion and contraction of said expansion means to accommodate a variety of vessel diameter sizes; and wherein said upper and lower spring assemblies comprise:
 (e) two groups of three or more spring slots formed at equal angular distances about the circumference of said shaft, one said group being immediately above said blade assembly and the other said group being immediately below said blade assembly, each said slot having an upper and lower edge;
 (f) a control wire in slidable communication within said shaft and operatively attached to said control means; and
 (g) three or more leaf springs within said spring slots further comprising:
   (i) a straight portion on one end of each said leaf spring secured to said control wire;
   (ii) a hook portion on the other end of each said leaf spring opposite said straight portion for pivotally biasing said leaf springs against said lower edges of said spring slots; and
   (iii) a spring body between said hook portion and said straight portion for protruding through said spring slot and making adjustable and expansive contact with said walls of said blood vessel as tension is applied to said control wire.

3. A device as described in claim 1, wherein said control means comprises:
 (a) a controller housing to which said shaft is removably attached at an end opposite said expansion means; and
 (b) a tension control means operatively attached to said controller housing for applying adjustable tension to said expansion means.

4. A device as described in claim 3, wherein said tension control means comprises:
 (a) a wire bore in axial alignment with said shaft formed in the front portion of said controller housing for allowing slidable communication with said control wire;
 (b) a screw bore in axial alignment with said wire bore formed in said controller housing;
 (c) a control screw in slidable communication with said screw bore and extending out from the rear end of said controller housing;
 (d) a wire holding means fixedly attached to said control screw for securing said control wire, and allowing tension to be applied to said control wire;
 (e) a control nut in threadable connection with the portion of said control screw extending from the rear of said controller housing for advancing said control screw through said controller housing and for applying tension to said control wire; and
 (f) a screw guide formed in said control screw for preventing rotation of said wire holding means as said control screw is advanced through said controller housing as tension is applied to said control wire.

* * * * *